(12) United States Patent
Wolf (10) Patent No.: US 7,372,584 B2
(45) Date of Patent: May 13, 2008

(54) DUAL PHOTO-ACOUSTIC AND RESISTIVITY MEASUREMENT SYSTEM

(75) Inventor: R. Gregory Wolf, Hackettstown, NJ (US)

(73) Assignee: Rudolph Technologies, Inc., Hackettstown, NJ (US)

( * ) Notice: Subject to any disclaimer, the term of this patent is extended or adjusted under 35 U.S.C. 154(b) by 98 days.

(21) Appl. No.: 11/104,093

(22) Filed: Apr. 11, 2005

(65) Prior Publication Data

US 2006/0227342 A1    Oct. 12, 2006

(51) Int. Cl.
*G01B 11/28* (2006.01)

(52) U.S. Cl. .................. 356/630; 356/632

(58) Field of Classification Search ........... 356/630, 356/632

See application file for complete search history.

(56) References Cited

U.S. PATENT DOCUMENTS

| | | | | |
|---|---|---|---|---|
| 3,416,078 A | * | 12/1968 | Ozias, Jr. et al. | 324/716 |
| 3,609,537 A | * | 9/1971 | Healy et al. | 324/601 |
| 3,676,775 A | * | 7/1972 | Dupnock et al. | 324/717 |
| 3,735,254 A | * | 5/1973 | Severin | 324/716 |
| 3,783,375 A | * | 1/1974 | Bennett | 324/601 |
| 4,710,030 A | | 12/1987 | Tauc et al. | 356/432 |
| 5,379,109 A | | 1/1995 | Gaskill et al. | 356/445 |
| 5,546,811 A | | 8/1996 | Rogers et al. | 73/800 |
| 5,693,938 A | | 12/1997 | Marchman et al. | 250/234 |
| 5,844,684 A | | 12/1998 | Maris et al. | 356/432 |
| 5,959,735 A | | 9/1999 | Maris et al. | 356/381 |
| 6,008,906 A | | 12/1999 | Maris | 356/432 |
| 6,038,026 A | | 3/2000 | Maris | 356/357 |
| 6,393,915 B1 | * | 5/2002 | Banet et al. | 73/579 |
| 7,050,160 B1 | * | 5/2006 | Johnson et al. | 356/73 |

\* cited by examiner

*Primary Examiner*—Roy M Punnoose
(74) *Attorney, Agent, or Firm*—Harrington & Smith, PC

(57) ABSTRACT

A measurement system for measuring aspects of a wafer combines an apparatus for performing a conductivity measurement, such as a four-point probe system, with apparatus for performing an optical measurement, such as a photoacoustic measurement system. Results are obtained and combined to provide comprehensive data sets describing the characteristics of the thin film substrate therein.

34 Claims, 7 Drawing Sheets

DUAL PHOTO-ACOUSTIC AND RESISTIVITY MEASUREMENT SYSTEM

TECHNICAL FIELD

The invention disclosed herein relates to the measurement of aspects of semiconductors, such as thickness of layers therein.

BACKGROUND OF THE INVENTION

Current methods for obtaining measured values for aspects of opaque thin films such as the thickness require a priori knowledge of one or more material properties of the thin film being measured. For example, a four-point probe measurement requires knowing the bulk resistivity of materials used in the film being measured to accurately calculate the thickness of the thin film. With this technique, four-point probe system is used to apply a current to an opaque film using two outer probes and simultaneously read the voltage drop across a portion of the film using the inner two probes. The current applied and the voltage measured together with the known bulk resistivity is used to calculate the thickness of the film. The calculation is simple, and described in detail in standard textbooks on semiconductor processing.

Though nominal values for materials currently being used in semiconductor applications are well known, these values are subject to variations in source materials used, variations in the process control parameters of the deposition tool used to form the film, etc.

U.S. Pat. No. 6,407,546, "Non-contact Technique for using an Eddy Current Probe for Measuring the Thickness of Metal Layers Disposed on Semiconductor Wafer Products," issued Jun. 18, 2002 to Le et al., describes another type of technique used for determining metal film thickness is the eddy current probe. This can be used to measure a metal's thickness as well as the sheet resistance from a known resistivity constant. However, it requires a calibration sample i.e. a sample that covers a wide variety of thickness range to generate baseline measurements. This information is used while measuring on the inspection sample whose thickness and sheet resistance are unknown. At the beginning of the calibration process, the eddy current probe is placed in contact with the calibration sample. The measurements are usually performed on a test wafer. There are also methods based on optical reflectivity techniques.

U.S. Pat. No. 5,228,776, "Apparatus for evaluating thermal and electrical characteristics in a sample," issued Jul. 20, 1993 to Smith et al., describes measuring changes in optical reflectivity caused by thermal waves to monitor variations in electrical conductivity and resistance as a method for evaluating the integrity of metal lines and vias in a semiconductor sample.

U.S. Pat. No. 6,054,868, "Apparatus and Method for Measuring a Property of a Layer in a Multilayered Structure," issued Apr. 25, 2000 to Borden et al., describes using a thermal conductance method for determining sheet resistivity of a conductive layer or thermal conductivity of a dielectric layer located beneath the conductive layer. According to Borden et al. the invention relies on focusing a heating beam on a conductive layer and modulating its power at a frequency that is predetermined to be low enough such that the heat generated by the beam transfers out of the heated region only by conduction. The power of a second beam, called as the probe beam, whose phase is modulated with modulation of the heating beam, reflected by the heated region is measured.

A photoacoustic film thickness system such as the MetaPulse™ system, available from Rudolph Technology Incorporated, can be used to measure thin film thicknesses on wafers. Such a system forms two optical beams: an excitation beam used to excite the surface of the film sample periodically, and a probe beam used to sense the reflectivity of the surface of the sample following each pulse from the excitation beam. The time interval between excitation of the film surface and the measurement of the reflectivity is varied in a controlled manner to obtain a measurement of the surface reflectance as a function of time. This data is analyzed using the acoustical impedance of each layer in the thin film stack on the wafer and a software program to calculate the thickness of each layer in the film stack.

Examples of optical systems are provided in the following U.S. Patents.

U.S. Pat. No. 6,008,906, "Optical Method for the Characterization of the Electrical Properties of Semiconductors and Insulating Films," issued Dec. 28, 1999 to Maris, describes a method for characterizing a sample that includes the steps of (a) providing a semiconductor material; (b) applying at least one of an electric field, a pulsed or cw light source, a change in temperature and/or a change in pump pulse intensity to the semiconductor material; (c) absorbing pump light pulses in a portion of the semiconductor material and measuring changes in optical constants as indicated by probe light pulses applied at some time t following the absorption of the pump light pulses; and (e) associating a measured change in the optical constants with at least one of a surface charge, dopant concentration, trap density, or minority carrier lifetime.

U.S. Pat. No. 4,710,030, "Optical Generator and Detector of Stress Pulses," issued Dec. 1, 1987 to Tauc et al., describes an optical stress pulse generation and detection system for non-destructively measuring physical properties of a sample. This system uses a pump beam having short duration radiation pulses having an intensity and at least one wavelength selected to non-destructively generate a stress pulse in a sample. The system directs the non-destructive pump beam to a surface of the sample to generate the stress pulse. The optical stress pulse generation and detection system also uses a probe radiation beam and guides the probe beam to a location at the sample to intercept the stress pulse. The change in optical constants induced by the stress pulse is detected by observing the probe beam after it intercepts the stress pulse.

U.S. Pat. No. 5,379,109, "Method and Apparatus for Non-Destructively Measuring Local Resistivity of Semiconductors," issued Jan. 3, 1995 to Gaskill et al., describes an apparatus for non-destructively measuring the resistivity of a semiconductor, such as InP. The system has light sources for illuminating a pre-selected portion of the semiconductor with first and second light beams, each of a pre-selected single wavelength. The first light beam operates to excite the semiconductor by photo-injecting carriers, and the second light beam bombards the local portion of the semiconductor with a pre-selected photon energy. The system measures a fractional change in reflectance of the second light beam responsive to the first light beam, and records this fractional change in reflectance for various values of photon energy of the second light beam, to generate a photoreflectance line-shape. The photoreflectance line-shape is used to calculate a photoreflectance line-shape phase angle, which is used to determine the resistivity of the pre-selected portion of the semiconductor.

U.S. Pat. No. 5,546,811, "Optical Measurements of Stress in Thin Film Materials," issued Aug. 20, 1996 to Rogers et al., describes a method for determining the residual stress in an unsupported region of a thin film. The method includes the steps of (a) optically exciting the film with a spatially and temporally varying optical excitation field to launch counter-propagating acoustic modes along at least one wave vector; (b) diffracting a portion of an optical probe field off the excited acoustic modes to generate a time-dependent signal field at the excitation wave vector; (c) detecting the signal field to generate a time-dependent, light-induced signal; (d) analyzing the light-induced signal to determine the frequencies of the acoustic modes; (e) partially determining the dispersion of at least one mode; and, (f) comparing the measured dispersion to that calculated using a mathematical model to allow the residual stress properties of the unsupported region of the film to be determined.

U.S. Pat. No. 5,693,938 "Optical Probe Microscope Having A Fiber Optic Tip That Receives Both A Dither Motion And A Scanning Motion, For Nondestructive Metrology Of Large Sample Surfaces," issued Dec. 2, 1997 to Marchman et al., describes an optical probe microscope that includes an optical fiber oriented in a vertical direction. The fiber has a tip that emits light onto a horizontal surface of a sample to be measured. This surface can have both desired and undesired departures from planarity. An electromechanical device for imparting dither motion to the fiber tip is superposed on another electromechanical device for imparting two-dimensional horizontal scanning motion to the fiber tip. The dither motion has a much higher frequency than that of the scanning motion. Between successive scans, another device moves the sample itself from one horizontal position to another. A microscope receives the optical radiation either transmitted or reflected by the sample surface. The microscope forms a (magnified) image of this received optical radiation on the surface of an optical image position detector. The surface of this detector has a relatively large area compared with that of the (magnified) image. The resulting electrical signal developed by the detector provides desired information concerning the scanning position of the fiber tip. Also, this electrical signal is processed and fed back to a vertical pusher that maintains constant the distance of the fiber tip from the sample surface.

U.S. Pat. No. 6,038,026, "Apparatus and Method for the Determination of Grain Size in Thin Films," issued Mar. 14, 2000 to Maris, describes a method for the determination of grain size in a thin film sample having steps of measuring first and second changes in the optical response of the thin film, comparing the first and second changes to find the attenuation of a propagating disturbance in the film and associating the attenuation of the disturbance to the grain size of the film. The second change in optical response is time delayed from the first change in optical response.

U.S. Pat. No. 5,959,735, "Optical Stress Generator and Detector," issued Sep. 28, 1999 to Maris et al., describes a system for the characterization of thin films, as well as interfaces between thin films, through measurements of their mechanical and thermal properties. In the system light is absorbed in a thin film or in a structure made up of several thin films, and the change in optical transmission or reflection is measured and analyzed. The change in reflection or transmission is used to give information about the ultrasonic waves that are produced in the structure. The information that is obtained can include (a) determination of the thickness of thin films with a speed and accuracy that is improved compared to earlier methods; (b) a determination of the thermal, elastic, and optical properties of thin films; (c) a determination of the stress in thin films; and (d) a characterization of the properties of interfaces, including the presence of roughness and defects.

U.S. Pat. No. 5,844,684, "Optical Method for Determining the Mechanical Properties of a Material," issued Dec. 1, 1998 to Maris et al., describes a system and method for characterizing a sample. The method includes steps of (a) acquiring data from the sample using at least one probe beam wavelength to measure, for times less than a few nanoseconds, a change in the reflectivity of the sample induced by a pump beam; (b) analyzing the data to determine at least one material property by comparing a background signal component of the data with data obtained for a similar delay time range from one or more samples prepared under conditions known to give rise to certain physical and chemical material properties; and (c) analyzing a component of the measured time dependent reflectivity caused by ultrasonic waves generated by the pump beam using the at least one determined material property. The first step of analyzing may include a step of interpolating between reference samples to obtain an intermediate set of material properties. The material properties may include sound velocity, density, and optical constants. In one embodiment, only a correlation is made with the background signal, and at least one of the structural phase, grain orientation, and stoichiometry is determined.

Though nominal values for materials currently being used in semiconductor applications are well known, these values are subject to variations in source materials used, variations in the process control parameters of the deposition tool used to form the film, etc.

Although the four-point probe system and photoacoustic film thickness systems provide a technique for measuring the thickness of a material, it would be advantageous to be able to verify test information as a means to insure accuracy.

SUMMARY OF THE INVENTION

The invention relates to an apparatus for making two independent measurements on the same measurement site on a wafer, also referred to herein as a "work piece," using both a four-point probe resistivity measurement system and a photoacoustic measurement system.

A first advantage of the present invention is that it allows two measurements to be performed on the measurement site on a wafer and then correlated. Data from the two tests may be correlated using known techniques, or with statistical tests as may be developed or preferable for the apparatus disclosed herein.

A second advantage of the present invention is that one measurement system may serve as a compliment to the other. For example, as the photoacoustic system 300 identifies a problem such as adhesions, inter-diffusion or missing layers in the layer interfaces, the four-point probe system 400 may be used to provide immediate diagnostic information, such as through conductivity measurements.

A third advantage of the present invention is that for ion implant applications, both photoacoustic and four-point probe tests can provide improved dose and energy measurements.

A fourth advantage of the present invention is that it allows the bulk conductivity to be determined through photoacoustic thickness measurements.

A fifth advantage of the present invention is that it allows the measurement of conductivity in a silicide substrate so that one can determine whether the proper phase had been formed.

Disclosed herein is an apparatus for measuring the thickness of a film on a wafer in a measurement system comprising a photo-acoustic measurement system and a four-point probe measurement system linked by means for positioning a measurement site on a wafer in the measurement region of the photo-acoustic measurement system and at a later time for positioning the measurement site in the measurement region of the four-point probe measurement system.

Also disclosed herein is method for operation of the apparatus.

An apparatus for measuring the thickness of a film on a wafer in a measurement system comprising: a photo-acoustic measurement system linked to means for positioning a measurement site on a wafer in the measurement region of the photo-acoustic measurement system and linked to means for inserting and causing a four-point probe head assembly of a four point probe measurement system to electrically contact the measurement site in the measurement region of the photo-acoustic measurement system.

Also disclosed herein is method for operation of the apparatus.

BRIEF DESCRIPTION OF THE DRAWING

The above set forth and other features of the invention are made more apparent in the ensuing Detailed Description of the Invention when read in conjunction with the attached Drawings, wherein.

DETAILED DESCRIPTION OF THE INVENTION

Disclosed herein are two embodiments of a dual photoacoustic and four-point probe measurement system. The two embodiments disclosed herein are considered to be illustrative and not limiting of the dual system. The dual system disclosed herein, and any variations thereof as may be realized by one skilled in the art, provide certain advantages such as improvements in the reliability of measurements of opaque films, and reductions in the number of steps to test a sample. Further advantages include providing a system wherein one type of measurement device may compliment another type, thereby providing a more comprehensive set of data.

The site where a measurement is taken is referred to herein as a "measurement site." Preferably, the measurement site is identical for measurements taken for purposes of correlating results from a first measurement subsystem with a second measurement subsystem. However, it is realized certain practical limitations or other concerns may make it difficult or nearly impossible to make measurements with one subsystem at exactly the same location as with another subsystem. Therefore, as used herein, a measurement site where multiple measurements are to be performed, can be accurately described as a set of locations that are within user defined tolerances for deviations in location coordinates. Where locations are within user defined tolerances, these locations effectively constitute a single "measurement site."

First Embodiment

Dual Side-by-Side Metrology System

Figure 1:
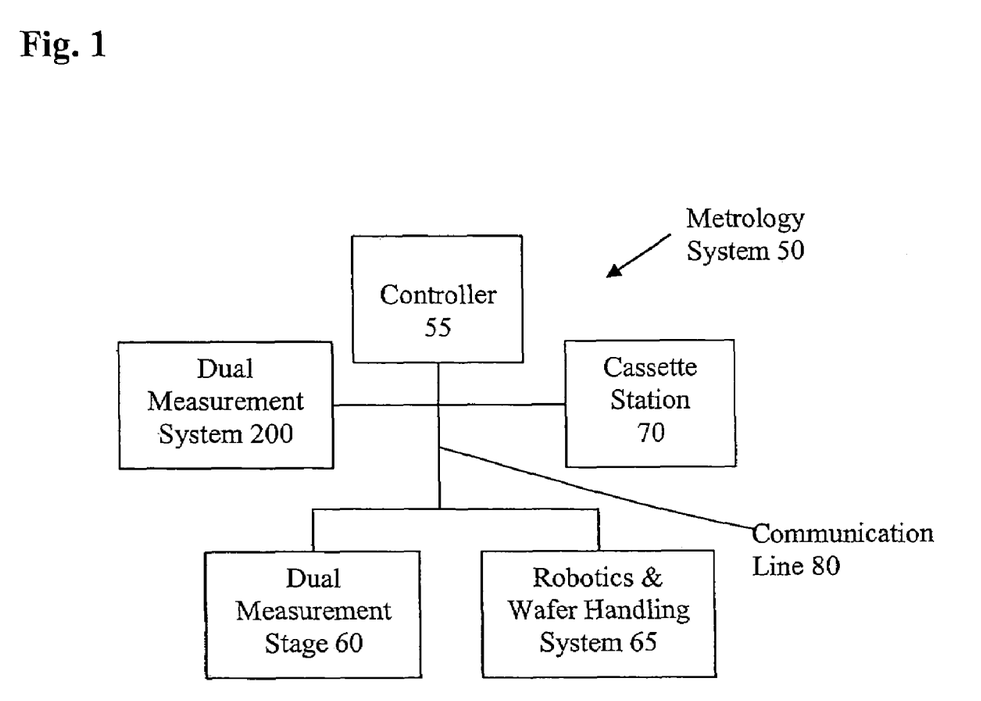
FIG. 1 is a block diagram showing the major components of a metrology system that includes a measurement stage.

As shown in FIG. 1, metrology system 50 includes a measurement stage 60 that moves the wafer under the probe for a series of measurements, a robotics and wafer handling system 65 that picks a wafer from a cassette, places it on stage 60 and returns it, a dual measurement system 200 that performs the measurements, a cassette station 70, a controller 55, and a communication line 80 that represents the various interconnections and interfaces. Controller 55, including a computing device with a processor and a memory, is electrically connected to dual measurement system 200, dual measurement stage 60, robotics and wafer handling system 65, and cassette station 70 with communication lines 80.

In operation, controller 55 sends an instruction to the robotics and wafer handling system 65 to extract a wafer from cassette station 70, and to position the wafer on the dual measurement stage 60. The controller 55 then issues commands to the measurement stage 60 to position the wafer into the measurement area of the measurement system so that measurements can be made at a predetermined measurement site on a work piece. The controller 55 then issues commands to the dual measurement system 200 to make a measurement and display the results of the measurement. Once the measurement is complete, controller 55 issues instructions to the robotics and wafer handling system 65 to return the wafer to the cassette station 70.

Preferably, the robotics and wafer handling system 65 includes a robot with a reticulated robot arm and an end-effector with which to hold a wafer so that it can be moved from the cassette to the dual measurement stage, and finally back to the cassette. Exemplary robotic systems suitable for use with the teachings herein are available from Western Servo Design, Kensington Laboratories, Fortrend Engineering, and MGI Electronics, and others.

Preferably, both the photoacoustic system and the four-point probe system are mounted adjacent to each other, or in a side-by-side arrangement. The systems are mounted so as to provide for measurement of aspects of the same location, or locations that are minimally spaced apart from each other, thus eliminating the need to align systems and perform a second measurement. Alternatively, the systems can be mounted in neighboring locations where the wafer is moved from one location to the other.

Figure 2:
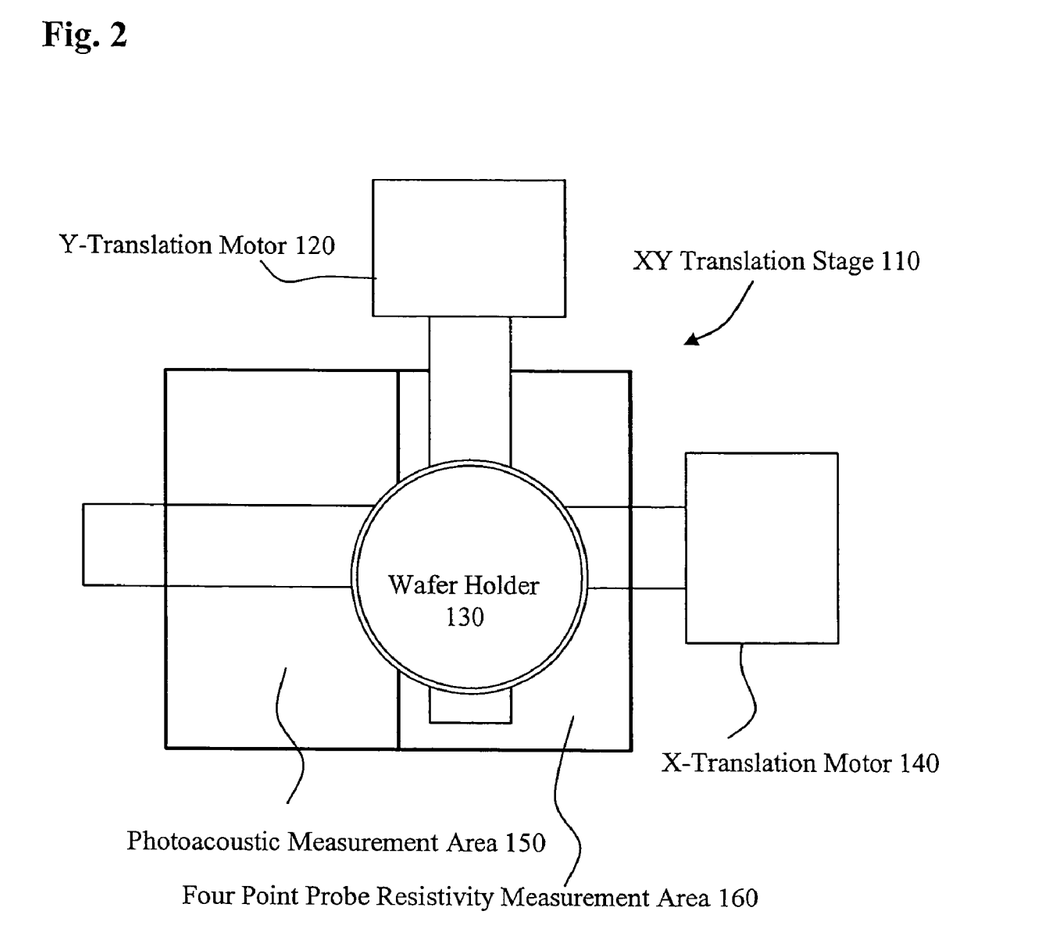
FIG. 2 illustrates one embodiment of a dual measurement stage for use in a side-by-side embodiment of the invention disclosed herein.

FIG. 2 describes the measurement stage portion of a metrology system 50 that includes a wafer holder 130 upon which the wafer is placed for measurements. Preferably, a precise XY-translation stage 110 provides wafer manipulation in two degrees of freedom. XY-translation stage 110 is driven by X-translation motor 140 and Y-translation motor 120. The XY-translation stage positions the wafer over the photoacoustic measurement area 150 and the four point probe resistivity measurement area 160. The stage is preferably linear, but a rotating or other type of stage may be substituted. Examples of automated stages suited for use with the teachings herein are available from Kensington Laboratories.

Distributed service facilities such as vacuum, compressed gas services, environmental controls and electrical power systems are preferably shared between the photoacoustic system, the four-point probe system, and the wafer handling/stage system. For example, a single clean air filtering system may be ducted to supply temperature and humidity control air to both measurement tools and the stage. Individual HEPA filters may be placed over each of the three areas or a single HEPA filter used and the clean air ducted to the three regions. In either case, the common air supply will preferably ensure ambient wafer temperature remains the same in both the photoacoustic and four-point probe regions.

Figure 3:
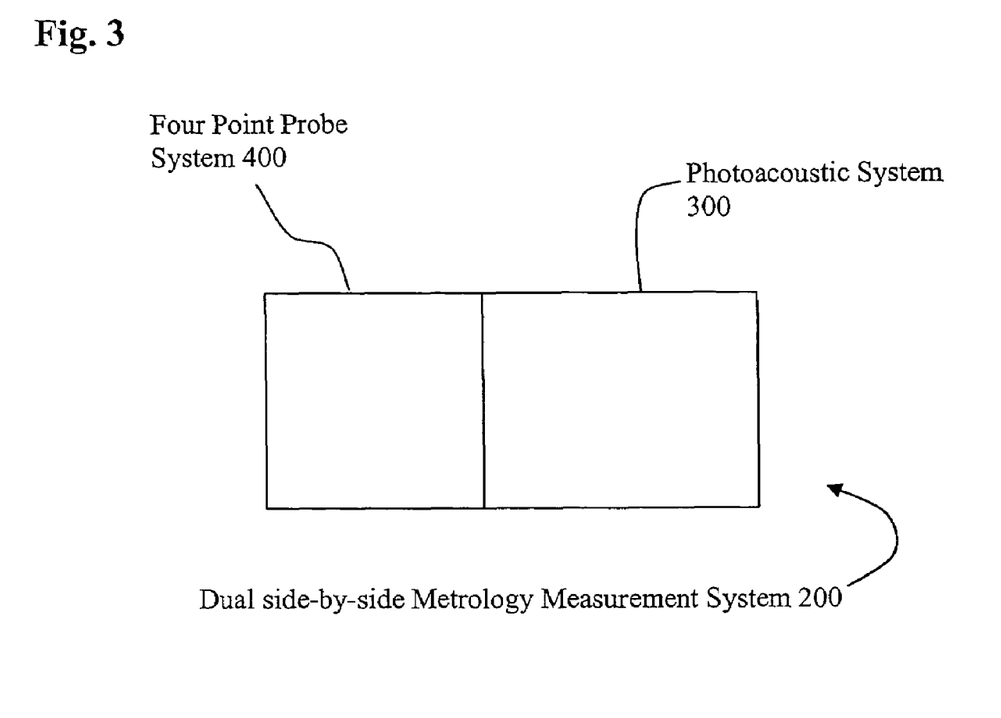
FIG. 3 illustrates one embodiment of a side-by-side metrology system.

FIG. 3 shows an overview of a side-by-side metrology system 200 containing two measurement apparatus. In the preferred embodiment, the side-by-side system 200 includes a four point probe system 400 and a photoacoustic system 300. Although aspects of the four point probe system 400 and the photoacoustic system 300 discussed herein relate to specific embodiments of such systems, these embodiments are considered to be only exemplary and not limiting of the invention. The first portion of the side-by-side system 200 to be discussed is the four point probe system 400.

Figure 4:
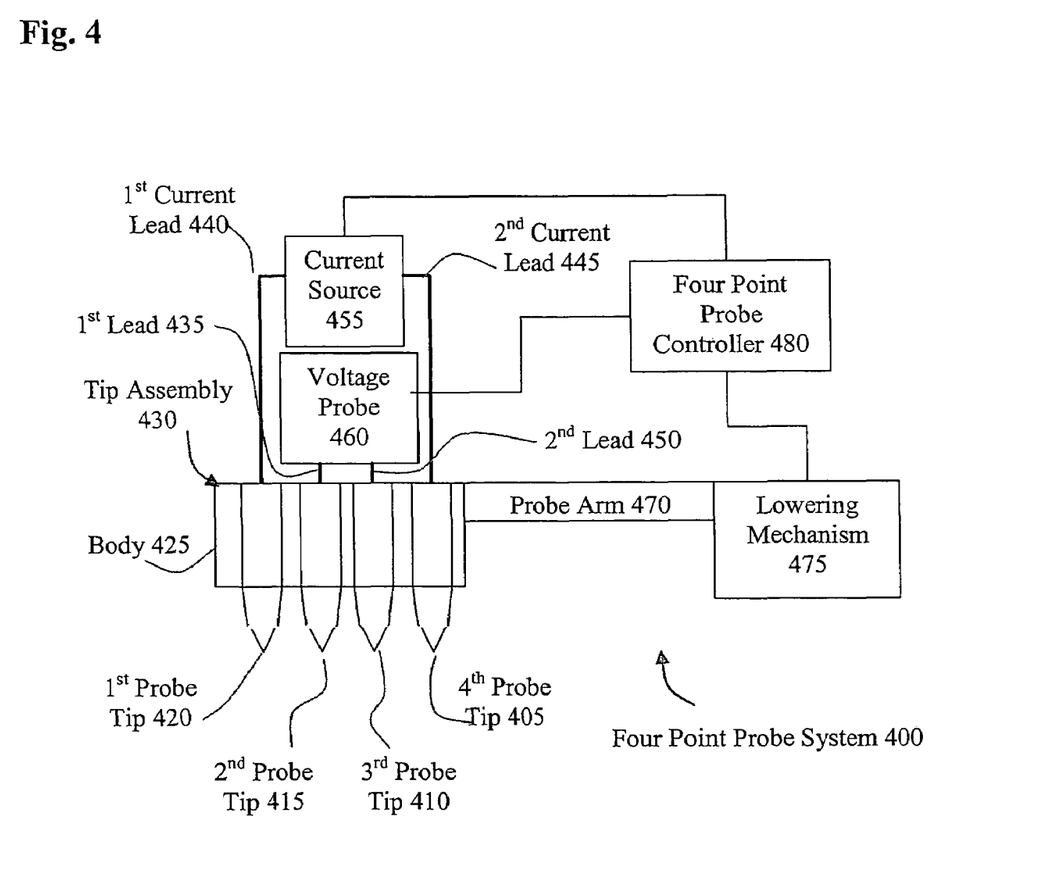
FIG. 4 illustrates aspects of a resistivity apparatus for use in the invention.

FIG. 4 illustrates a four-point probe system 400 that includes a four-point probe controller 480, a current source 455, a voltage probe 460 with a first lead 435 and second lead 450, a tip assembly 430, a probe arm 470, and a lowering mechanism 475. The tip assembly 430 includes a body 425, a first probe tip 420, a second probe tip 415, a third probe tip 410, and a fourth probe tip 405. The four probe tips are configured in a straight line. Exemplary probe tip assemblies, including probe tips with spacing suitable for semiconductor applications (having approximately 100 um separation), are manufactured by Jandel Engineering LTD. Individual probe tips are available from Allessi Industries, and Signaltone.

Preferably, the probe tips are mounted in the tip assembly 430 so that all four tips protrude the same distance. The tip assembly 430 is connected to a probe arm 470. The probe arm 470 is connected to a lowering mechanism 475. The four-point probe controller 480, which may be part of system controller 55, is electrically connected to the lowering mechanism 475, the current source 455, and the voltage probe 460. The current source 455 has a first current lead 440 that is connected to the first probe tip 420. The current source 455 has a second current 445 lead that is connected to the fourth probe tip 405. The voltage probe 460 has a first lead 435 that is connected to the second probe tip 415 and a second lead 450 that is connected to the third probe tip 410.

The controller 480 is loaded with data indicating the bulk resistivity of the top layer being measured, and a value for an appropriate amount of current with which to make a four-point probe measurement. In operation, upon command of the controller 55, the four-point probe controller 480 instructs the lowering mechanism 475 to lower the tip assembly 430 to a predetermined position that allows the four probe tips to contact the surface of the wafer being measured. Once lowered into position, the four-point probe controller 480 instructs the current source 455 to apply current to the wafer. The current flows via the first current lead 435 through the first probe tip 420 and into the wafer. The current returns via the fourth probe tip 405 and the second current lead 450 to the current source 455. While current flows, the four-point probe controller 480 instructs the voltage probe 460 to sense the voltage between the second probe tip 415 and the third probe tip 410. The four-point probe controller 480 then sends the voltage measurement back to the controller. A program running in the controller 480 then calculates the thickness of the layer in which the four-point probe 400 was applied using the voltage measurement, the value of the current applied to the sample and the bulk resistivity.

The steps of making a measurement, recording the measurement, and calculating a result of the measurement using a four-point probe system are well known. For example, engineering textbooks on semiconductor processing discuss methods for extracting film thickness values from four-point probe measurements. Preferably, probe tips 410 and 415 are separated by a space that has room for the photoacoustic measurement apparatus to pass a beam through to the measurement spot.

Figure 5:
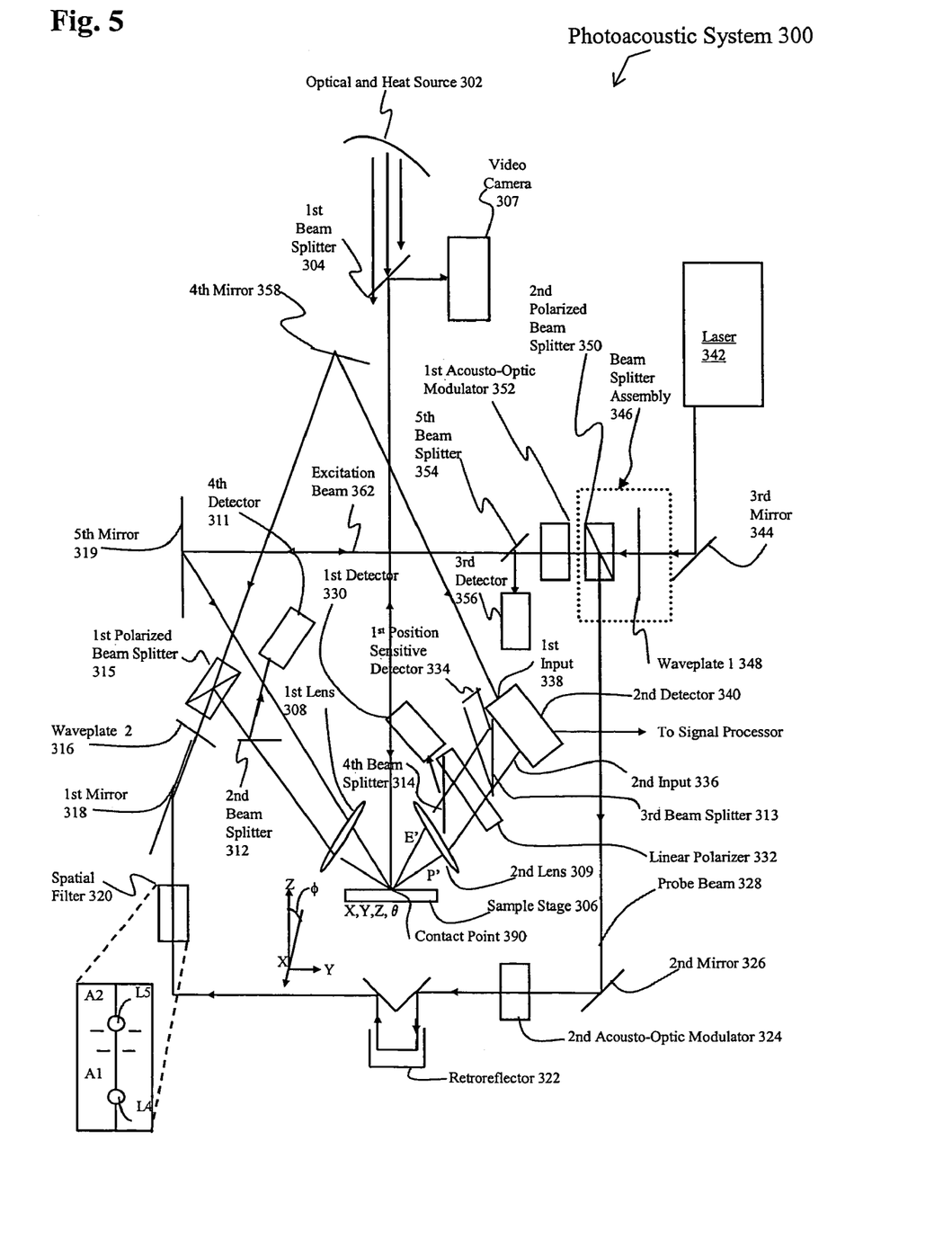
FIG. 5 illustrates aspects of a photoacoustic metrology system suited for use in this invention.

FIG. 5 illustrates a photoacoustic system 300. The photoacoustic system 300 preferably includes an optical/heat source 302, a laser 342, a video camera 307, a sample stage 306, a first beam splitter 304, a second beam splitter 312, a pump-probe beam splitter assembly 346, a first acousto-optic modulator 352, and a second acousto-optic modulator 324. The pump-probe beamsplitter assembly 346 includes a waveplate 1 348 and a second polarized beam splitter 350. Additionally, the photoacoustic system 300 includes a spatial filter 320, a retroreflector 322, a wave plate 2 316, a first polarized beam splitter 315, and a second detector 340 with first input 338 and second input 336.

Additionally, the photoacoustic system 300 includes a fourth detector 311, polarizer 332, a first lens 308, a second lens 309, a third beam splitter 313, a fourth beam splitter 314, a first position sensitive detector (PSD) 334, a third detector 356, a fifth beam splitter 354, a first polarized beam splitter 315 and a first detector 330. The photoacoustic system 300 also includes first mirror 318, second mirror 326, third mirror 344, fourth mirror 358, and fifth mirror 319. In addition, the photoacoustic system 300 includes a probe beam 328 and an excitation beam 362 (the terms "excitation beam" and "pump beam" are used interchangeably).

The laser 342 is preferably a titanium-sapphire laser operating at 80 MHz and emitting light at a wavelength of 800 nm. The laser 342 can also be alternatively configured with a frequency doubling crystal to emit light at 300 nm.

In operation, the probe beam 328 and the excitation beam 362 are reflected from contact point 390 forming beams P' and E' respectively. Beams P' and E' propagate through second lens 309 and through polarizer 332 and are then split by third beam splitter 313. Third beam splitter 313 provides beams P' and E' to first position sensitive detector 334.

Additionally, optical/heat source 302, which functions as a variable high-density illuminator, provides illumination for a video camera 307 and acts as a sample heat source for temperature-dependent measurements under computer control. The video camera 307 provides a displayed image for an operator or appropriate pattern recognition software, and facilitates the setup of the measurement system.

The sample stage 306 is preferably a multiple-degree of freedom stage that is adjustable in height (z-axis), position (x and y-axes), and tilt (theta), and allows motor controlled positioning of a portion of the sample relative to the pump and probe beams. The z-axis is used to translate the sample vertically into the focus region of the pump and probe, the x- and y-axes translate the sample parallel to the focal plane, and the tilt axes adjust the orientation of the stage sample stage 306 to establish a desired angle of incidence for the probe beam.

First beam splitter 304 is a broadband beam splitter that directs video and a small amount of laser light to the video camera 307. The video camera 307 and local processor can be used to automatically position the pump and probe beams on a measurement site.

The pump-probe beam splitter assembly 346 splits an incident laser beam pulse (preferably of picosecond or shorter duration) into pump and probe beams, and includes a rotatable half-waveplate 1 348 that rotates the polarization of the un-split beam. Waveplate 1 348 is used in combination with second polarized beam splitter 350 to effect a continuously variable split between pump and probe power. This split may be controlled by the controller 55 (shown in FIG. 1) and a motor (not shown) to achieve an optimal signal-to-noise ratio for a particular sample. The appropriate split depends upon factors such as the reflectivity and roughness of the sample. Adjustment is effected by having a motorized mount rotate waveplate 1 348 under computer control.

A first acousto-optic modulator 352 chops the pump beam at a frequency of about 1 MHz. A second acousto-optic modulator 324 (AOM) chops the probe beam at a frequency that differs by a small amount from that of the first pump modulator acousto-optic modulator 352.

A spatial filter 320 is used to preserve at its output a substantially invariant probe beam profile, diameter, and propagation direction for an input probe beam. Among other things, the input probe beam 328 may vary due to the action of the mechanical delay line shown as the retroreflector 322. The spatial filter 320 includes a pair of apertures A1 and A2, and a pair of lenses L4 and L5. An alternative embodiment of the spatial filter 320 incorporates an optical fiber.

Waveplate 2 316 is a second adjustable half-waveplate that functions in a similar manner, with first polarized beam splitter 315, to the waveplate 1 348 and second polarized beam splitter 350 of the beam splitter assembly 346. With waveplate 2 316, the intent is to vary the ratio of the part of the probe beam impinging on the sample to that of the portion of the beam used as a reference (first input 338 of second detector 340). Waveplate 2 316 may be motor controlled to achieve a ratio of approximately unity. The electrical signals produced by the beams are subtracted, leaving only the modulated part of the probe beam 328 to be amplified and processed. Second beam splitter 312 is positioned so as to direct a small fraction of probe beam 328 onto fourth detector 311, which measures a signal proportional to the probe beam 328 intensity.

The linear polarizer 332 is employed to block scattered pump light polarization, and to pass the probe beam 328. First lens 308 and second lens 309 are pump and probe beam focusing and collimating objectives, respectively. Third beam splitter 313 is used to direct a small part of the pump and probe beams onto a first position sensitive detector 334 that is used for auto focusing, in conjunction with controller 55 (shown in FIG. 1) and movements of the sample stage 306. The first position sensitive detector 334 is employed in combination with controller 55 (shown in FIG. 1) and the computer-controlled sample stage 306 (tilt and z-axis) to automatically focus the pump and probe beams onto the sample to achieve a desired focusing condition.

The steps of making a measurement, recording the measurement, and calculating a result of the measurement using a photo-acoustic system are well known. For example, in a photoacoustic measurement, the process of calculating a result is discussed in U.S. Pat. No. 4,710,030 issued Tauc, et al.

Second Embodiment

Integrated Metrology System

A second embodiment of a dual measurement system apparatus is now presented. The second embodiment preferably makes use of the foregoing exemplary four point probe system 400 and the photoacoustic system 300.

Figure 6:
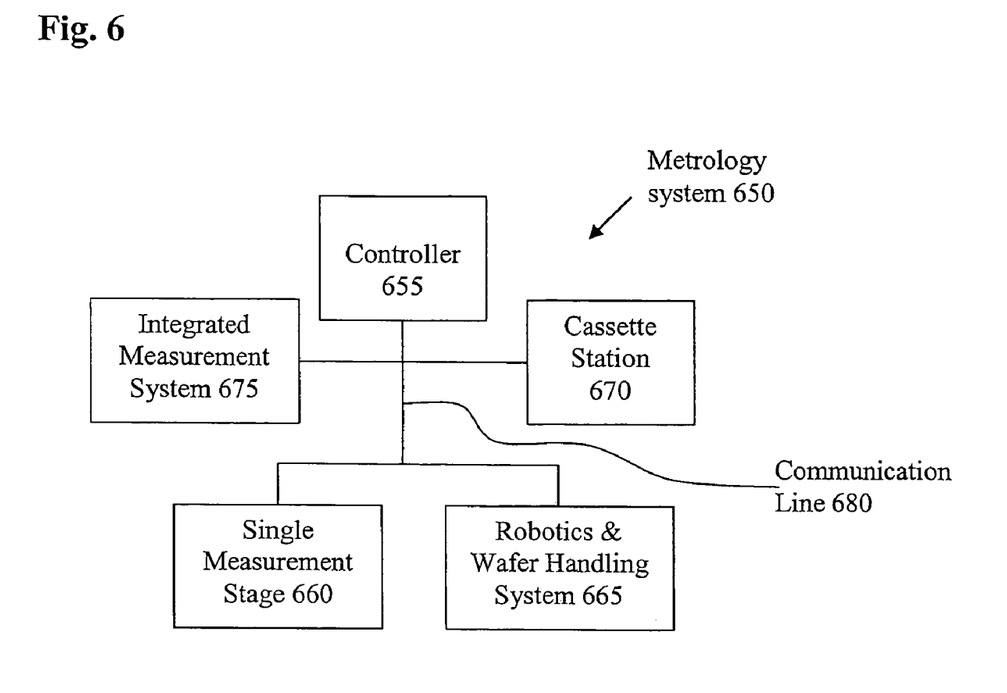
FIG. 6 illustrates major components in an integrated metrology system.

As shown in FIG. 6, the metrology system 650 includes a dual measurement stage 660, a robotics and wafer handling system 665, a single measurement system 675, a cassette station 670, a controller 655, and a communication line 680.

The controller 655 is electrically connected to the dual measurement system 675, the dual measurement stage 660, the robotics and wafer handling system 665, and the cassette station 670 with communication lines 680.

Controller 655 includes a computing device with a processor and a memory (not shown). In operation, controller 655 sends an instruction to the robotics and wafer handling system 665 to extract a wafer from cassette station 670, and to position the wafer on the dual measurement stage 660. The controller 655 then issues commands to the measurement stage 660 to position the wafer relative to the measurement system 675 so that measurements can be made at a predetermined location. The controller 655 then issues commands to the dual measurement system 675 to make a measurement and display the results of the measurement. Once the measurement is complete, controller 655 issues instructions to the robotics and wafer handling system 665 to return the wafer to the cassette station 670.

In one embodiment, there is enough space between probes for the beams of light from the photoacoustic system 300 to pass unperturbed. In another embodiment, the probe body 425, shown in FIG. 4, pivots out of the way of the photoacoustic system apparatus 300.

In preferred embodiments, the robotics and wafer handling 665 system includes a robot with a reticulated robot arm and an end-effector with which to hold a wafer so that it can be moved from the cassette to the dual measurement stage, and finally back to the cassette. Aspects of robotic systems have been discussed above.

Figure 7:
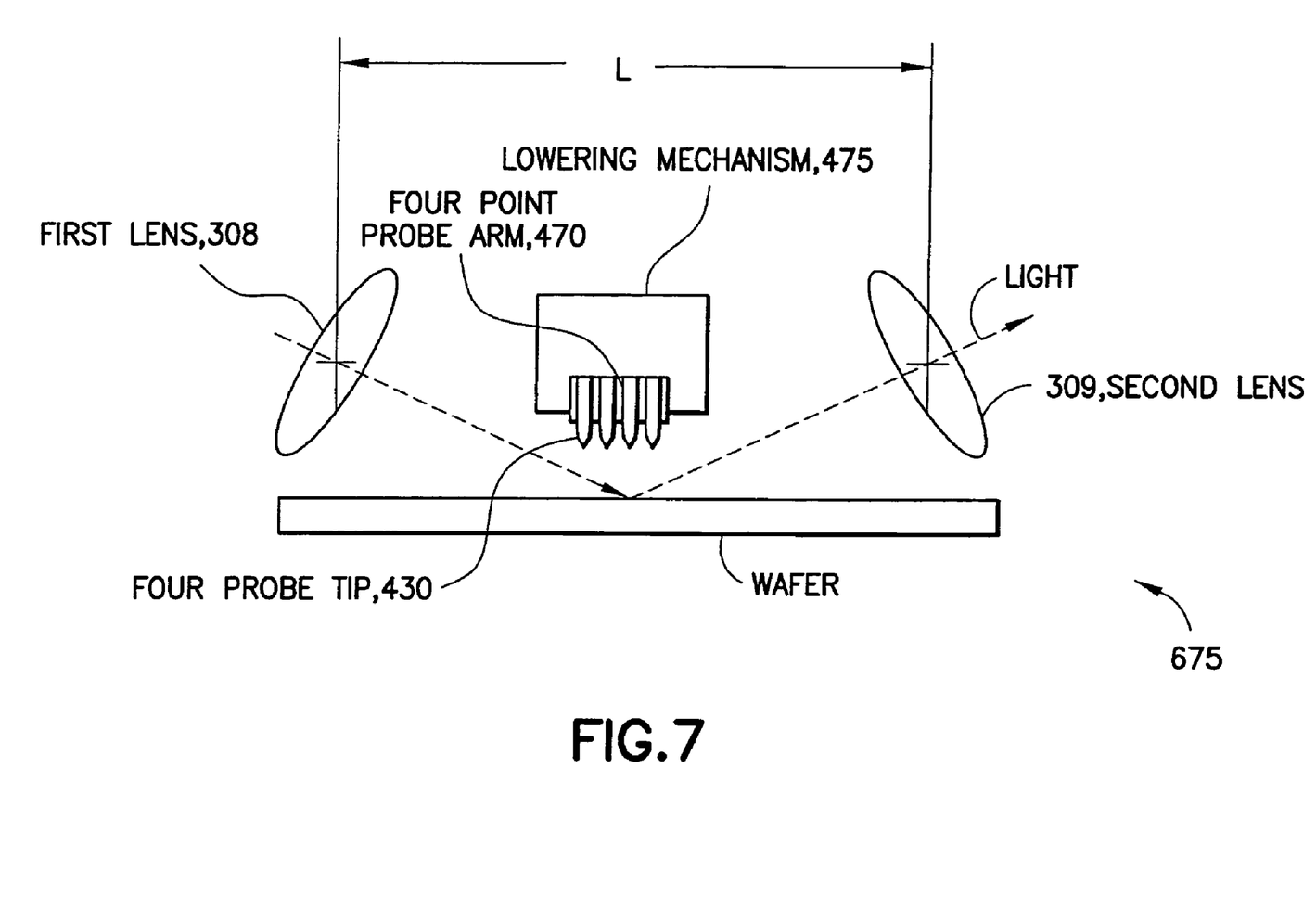
FIG. 7 illustrates components an integrated four-point probe and photoacoustic metrology system.

FIG. 7 illustrates aspects of the integrated system. The integrated test system 675 includes a photoacoustic film thickness measurement system 300 as described in FIG. 5, represented herein by first lens 308 and second lens 309 and the dotted line indicating the optical axis of the photoacoustic system 300. Distance L between the first lens 308 and the second lens 309 is preferably between about two to four centimeters. The dotted line arrow indicates the optical axis of the photoacoustic system 300. FIG. 7 also illustrates the four-point probe tip assembly 430 of the four-point probe system 400, where the remaining elements of the system 400, as described in FIG. 4, are not shown to simplify the illustration.

The four-point probe system 400 and the photoacoustic film thickness system 300 are used to make sequential measurements at the same site on the same wafer while the wafer is held stationary in a single test position.

The photoacoustic system 300 may be modified to arrange structural elements to accommodate mechanical insertion and lowering of the four-point probe head, or tip assembly 430 into position for making a measurement. This method is preferred over moving the optics of the photoacoustic system 300 because of the sensitivity of lens alignment to measurement accuracy. Preferably, either a horizontal injection or vertical lowering of the tip assembly 430, or a horizontal, cantilever lowering is used. When using cantilever lowering, it is preferable that the probe tips are oriented tangentially to the arc of the cantilever and the arc is small.

Operation

Operation of the apparatus of the metrology measurement systems disclosed herein typically involves making a series of measurements at various measurement sites on a wafer and processing the measurement results. The results may be useful for evaluations such as, and not limited to: verifying the thickness of the material being measured; assessing thickness in new measurements; or adjusting measured results in accordance with statistical tests for qualifying the separate measurements.

Measurements using the first embodiment of a dual measurement system, that of a side-by-side apparatus, may include:

(a) transferring a wafer from the cassette to the wafer holder;
(b) positioning a selected site on the wafer in the measurement area of the photoacoustic system;
(c) making a photoacoustic measurement on the selected site;
(d) calculating the thickness of the film on the selected site based on the photoacoustic measurement;
(e) positioning the selected site on the wafer in the measurement area of the four-point probe system;
(f) making the four-point probe measurement on the selected measurement site;
(g) calculating the thickness of the film on the selected site based on the four-point probe measurement;
(h) selecting and positioning a new site on the wafer in the photoacoustic area of the tool and repeating steps (c) through (h) until all sites to be measured have been measured;
(i) determining a standard correlation coefficient between the photoacoustic and four-point probe thickness by selected site;
(j) reporting the thickness measurements and correlation coefficient; and
(k) transferring the wafer back to the cassette.

Note that certain steps, such as steps c-g, are important to the measurement process, while aspects of the other steps may be varied or omitted as deemed appropriate.

Since contact or penetration into the sample with the tip assembly 430 could damage the surface, it is preferred to perform the photoacoustic measurement first. It should be noted that care must also be taken when using the photoacoustic system 300, such as to control the power level of the excitation beam 362 and the probe beam 328.

The correlation coefficient may be made using any least mean square fit type algorithm, any number of which may be found in standard textbooks of numerical analysis methods. The user sets acceptable values of correlation coefficient dependent upon a history of measurements made on similar wafers of a particular film type and thickness. The actual value reported may be a simple average of the results of the two techniques or any statistical manipulation of the thickness data by the user.

In some embodiments of methods for using the system disclosed herein, when the statistic, such as the correlation coefficient, exceeds a predetermined value, then the user will require re-calibration or other adjustment of the apparatus.

Other statistical tests and schemes may be employed or substituted to evaluate the data produced by the apparatus, or to evaluate aspects of the apparatus (e.g. calibration).

It is considered to be inherent that as aspects of the photoacoustic system 300 and the four-point probe system 400 are fundamentally different, certain aspects of measurement will affect one system more than the other (in certain instances). For example, aspects such as, and not limited to, impurity profiles, grain size, micro crystal structure and size, and surface films may produce varying results, and therefore, one to one correspondence in the thickness measured by each technique may not always be realized. It is expected that these differences may or will appear in measurements on a site-to-site basis.

The same variations apply to the substrate upon which the film is deposited. Additionally, ambient conditions such as temperature and humidity affect the two techniques differently. Further, four-point probe measurements are sensitive to the probe tip diameter, tip spacing, tip pressure, and tend to change with use.

The method for performing measurements with an integrated apparatus include:

(a) transferring a wafer from the cassette to the wafer holder;
(b) positioning a selected site on the wafer in the measurement area of the tool area of the system;
(c) making a photoacoustic measurement on the selected site;
(d) calculating the thickness of the film on the selected site based on the photoacoustic measurement;
(e) making the four-point probe measurement on the selected measurement site;
(f) calculating the thickness of the film on the selected site based on the four-point probe measurement;
(g) selecting and positioning a new site on the wafer in the measurement area of the tool and repeating steps (c) through (g) until all sites to be measured have been measured;
(h) determining a standard correlation coefficient between the photoacoustic and four-point probe thickness by selected site;
(i) reporting the thickness measurements and correlation coefficient; and
(j) transferring the wafer back to the cassette.

Note again that certain steps, such as steps c-f, are important to the measurement process, while aspects of the other steps may be varied or omitted as deemed appropriate.

Correlation of the measurements from the two techniques and factors that prevent one to one correlation between the four point probe system 400 and the photoacoustic system 300 have been discussed above.

One skilled in the art will recognize that the teachings herein are illustrative of dual measurement system, and are therefore not to be considered limiting. For example, it should be recognized that both the conductivity measurement apparatus and the photoacoustic measurement apparatus are assembled from various components, and that components thereof may be advantageously replaced for improved results. Therefore, at least other embodiments of photoacoustic or conductivity systems are considered within the teachings herein. Furthermore, it is considered that as other apparatus may be devised to address the functions of these systems, that these apparatus will likewise be within the teachings herein.

What is claimed is:

1. A measurement system comprising:
a first subsystem for performing an optical measurement of a measurement site on a wafer using sequential illumination along at least one beam path;
a second subsystem mounted adjacent to the first subsystem, the second subsystem for performing an electrical measurement of conductivity on the measurement site using a set of probes supported by a probe support; and
a controller for operating a translation stage to align the measurement site with the first subsystem and the second subsystem;

wherein the first subsystem and the second subsystem are independently used to calculate a property of the wafer.

2. A system as in claim 1, where the first subsystem and the second subsystem share services comprising at least one of vacuum, compressed gas, environmental controls and electrical power.

3. A system as in claim 1, the first subsystem comprises a photoacoustic measurement system.

4. A system as in claim 1, the second subsystem comprises a four point probe system.

5. A system as in claim 1, further comprising the translation stage that is configured to move the wafer between a location in the first subsystem suitable to allow the first subsystem to perform the optical measurement on the measurement site and between a location in the second subsystem suitable to allow the second subsystem to perform the electrical measurement on the measurement site.

6. A system as in claim 1, wherein the controller aligns the measurement site for the first subsystem and the measurement site for the second subsystem to be at substantially the same location.

7. A measurement system comprising:
a first subsystem for performing an optical measurement using sequential illumination along at least one beam path of a measurement site on a wafer; and
a second subsystem for performing an electrical measurement of conductivity on the measurement site using a set of probes supported by a probe support; in which
the probe support comprises means for moving said set of probes from a probe measurement position that would interfere with the at least one beam path during optical measurement to a non-blocking position that does not interfere with the at least one beam path during optical measurement;
wherein the first subsystem and the second subsystem are independently used to calculate a property of the wafer.

8. A system as in claim 7, the first subsystem comprises a photoacoustic measurement system.

9. A system as in claim 7, the second subsystem comprises a four point probe system.

10. A system as in claim 7, wherein the probe support is adapted for insertion into position for making a measurement.

11. A system as in claim 10, wherein insertion comprises one of horizontal injection, vertical lowering and cantilever lowering.

12. A system as in claim 7, wherein the measurement site for the first subsystem and the measurement site for the second subsystem are at substantially the same location.

13. A method of measuring a wafer comprising:
positioning a first measurement site of a set of measurement sites on the wafer in a measurement area of a first subsystem for performing an optical measurement using sequential illumination along at least one beam path striking the wafer;
using the first subsystem, making an optical measurement on the first measurement site to produce optical measurement data;
using a second subsystem, making a conductivity measurement on the first measurement site to produce conductivity measurement data;
independently calculating a property of the wafer from the optical measurement data;
independently calculating the same property of the wafer from the conductivity measurement data;
correlating the independently calculated properties to form a result; and
repeating the positioning, the making an optical measurement, the making a conductivity measurement, the calculations and the correlating until results are formed for all measurement sites.

14. A method as in claim 13, wherein making the optical measurement comprises operating a photoacoustic measurement system.

15. A method as in claim 13, wherein making the conductivity measurement comprises operating a four point probe system.

16. A method as in claim 13, further comprising using a robotic system for at least one of transferring the wafer and positioning at least one of the measurement sites.

17. A method as in claim 13, further comprising determining a statistic for qualifying at least one result.

18. A method as in claim 17, wherein the statistic is a correlation coefficient.

19. A method as in claim 17, further comprising:
using the statistic to adjust the results.

20. A method as in claim 13, further comprising: using the statistic to determine that at least one of the first subsystem or the second subsystem should be adjusted.

21. A method as in claim 13, further comprising positioning the measurement site in the measurement area of the second subsystem prior to the making a conductivity measurement.

22. A method as in claim 13, wherein each of the results is representative of the thickness of at least one film on the wafer at the measurement site.

23. A method as in claim 13, further comprising performing an evaluation using the results.

24. A method as in claim 23, wherein the each of the results is indicative of a thickness of a film on the wafer at the measurement site, and wherein performing an evaluation comprises at least one of the following:
verifying a thickness of the film;
assessing thickness determined through performing additional measurements using the first and second subsystems; or
adjusting measured results in accordance with at least one statistical test.

25. A method as in claim 13, wherein the first measurement site is positioned so that the first subsystem and second subsystem produce data corresponding to substantially the same location.

26. A method for operating a dual measurement system, the method comprising:
making a measurement with a photoacoustic system at a measurement site for independently identifying information regarding at least one property of the measurement site;
making a measurement with a conductivity system; and
evaluating the at least one property of the measurement site using at least the information and data from the measurement made with the conductivity system.

27. A method as in claim 26, wherein the at least one property comprises at least one of adhesion, inter-diffusion and a missing layer.

28. A method as in claim 26, wherein the information comprises bulk conductivity of the measurement site.

29. A method as in claim 26, wherein evaluating comprises determining if a proper phase of a substrate has been formed.

30. A method as in claim 26, wherein the first measurement site is positioned so that the photoacoustic system and the conductivity system make measurements at substantially the same location.

31. An apparatus for determining a thickness of a film on a wafer, comprising:

a photo-acoustic measurement system and a four-point probe measurement system linked by means for positioning a measurement site on a wafer in the measurement region of the photo-acoustic measurement system and at a later time for positioning the measurement site in the measurement region of the four-point probe measurement system; wherein data provided by the photo-acoustic system is independently used to determine the thickness, the data from the four-point probe system is independently used to determine the thickness, and the determinations of thickness are correlated.

32. An apparatus as in claim 31, wherein the positioning means positions the measurement site for the photoacoustic measurement system and the measurement site for the four-point probe measurement system to be at substantially the same location.

33. An apparatus for determining the thickness of a film on a wafer, comprising:

a photo-acoustic measurement system linked to means for positioning a measurement site on a wafer in the measurement region of the photo-acoustic measurement system and linked to means for inserting and causing a four-point probe head assembly of a four point probe measurement system to electrically contact the measurement site in the measurement region of the photo-acoustic measurement system; wherein data provided by the photo-acoustic system is independently used to determine the thickness, the data from the four-point probe system is independently used to determine the thickness, and the determinations of thickness are correlated.

34. An apparatus as in claim 33, wherein the positioning means positions the measurement site for the photoacoustic measurement system and the measurement site for the four-point probe measurement system to be at substantially the same location.

* * * * *